US00PP07840P

United States Patent [19]

Kientzler

[11] Patent Number: Plant 7,840

[45] Date of Patent: Mar. 24, 1992

[54] NEW GUINEA IMPATIENS PLANT NAMED ANAEA

[75] Inventor: Ludwig Kientzler, Gensingen, Fed. Rep. of Germany

[73] Assignee: Paul Ecke Ranch, Inc., Encinitas, Calif.

[21] Appl. No.: 577,136

[22] Filed: Sep. 5, 1990

[51] Int. Cl.[5] ..... A01H 5/00

[52] U.S. Cl. ..... Plt./68

[58] Field of Search ..... Plt./68, 87.6

[56] References Cited

U.S. PATENT DOCUMENTS

P.P. 6,683 3/1989 Kientzler ..... Plt. 68

*Primary Examiner*—Howard J. Locker

*Attorney, Agent, or Firm*—Foley & Lardner

[57] ABSTRACT

An Impatiens plant named Anaea having dark velvety red flowers, dark green leaves, early flowering and long lasting flowers, floriferous habit, and a strong and compact growth habit.

1 Drawing Sheet

The present invention relates to a new and distinctive cultivar of Impatiens plant known by the cultivar name Anaea, botanically known as Impatiens, and commercially known as New Guinea Impatiens.

Anaea was developed by the applicant through a controlled breeding program in Gensingen, Federal Republic of Germany. The male or pollen parent was identified by the cultivar designation B 95, and the female or seed parent was identified by the cultivar designation C 77. Anaea was discovered and selected as one flowering plant with the progeny of the cross by the applicant in a controlled environment in Gensingen, Federal Republic of Germany.

The first act of asexual reproduction of Anaea was accomplished when terminal or stem cuttings were taken from the initial selection by applicant in a controlled environment in Gensingen, Federal Republic of Germany. Horticultural examination of selected plants of Anaea has demonstrated that the combination of characteristics as herein disclosed for Anaea are firmly fixed and are retained through successive generations of asexual reproduction.

Anaea has not been observed under all possible environmental conditions. The phenotype may vary significantly with variations in environment such as temperature, light intensity, soil conditions, nutrient feeding, and day length.

The following characteristics distinguish the new Impatiens from both its parent varities and other cultivated impatiens of this type known and used in the floriculture industry within the knowledge of applicant:

1. Dark, velvety red flowers.
2. Dark green, non-variegated leaves. The contrast of the colors of the foliage and flowers is striking.
3. The plant flowers early and is very floriferous.
4. The flowers are long-lasting.
5. The growth habit is strong and compact, with excellent branching.

The accompanying colored photograph illustrates in perspective view the overall appearance of this cultivar, with colors being as true as it is reasonably possible to obtain in a colored reproduction of this type.

The following is a detailed description of Anaea based on plants produced under commercial practice in Encinitas, Calif. Unrooted cuttings were rooted under intermittent mist, and the plants subsequently transplanted to 15 cm. pots. Flowering commenced in November 1989. Cuttings were taken from these established plants in January 1990, rooted and planted in 10 cm. pots. After 5–6 more weeks the plants were nicely proportioned for 10 cm. pots, and data was collected. Most of the data which follows was collected between Apr. 1–15, 1990 in Encinitas, Calif. The measurements and description of foliage were taken from fully expanded leaves.

Color references are made to The Royal Horticultural Society Colour Chart except where general terms of ordinary dictionary significance are used. Color chart correlations were made under indirect natural light conditions, with the leaves and flowers being compared to the R.H.S. colour Chart on a north exposure.

Parentage: Seedling from cross pollination of male parent B 95 with female parent C 77.

Propagation:

*Type cutting.*—Tip cutting. Stems 2–3 cm. long will develop to 4–5 cm. After 21 days in propagation.

*Time to initiate roots.*—8–10 days at 23° C. Nicely developed root mass in 18–21 days.

*Rooting habit.*—Numerous, fibrous advantitious roots from the stem.

Plant description:

*Form.*—Symmetrical, bush shaped, flowering herb, with self-branching characteristics giving the plant a full appearance.

*Habit of growth.*—Self-branching, compact habit, producing whorls of leaves and flowers on branched stems. Growth is indeterminate and flowering is continuous.

*Size.*—When grown as single plants in 10 cm pots with the plants not being pinched, plants in full flower are 23–25 cm in height (including the pot), 26–28 cm in width or spread, and have an average number of 8 strong branches.

*Foliage description.*—Leaves are simple. Lower leaves on stem are opposite. Higher leaves in whorls of 3 to mostly 5, and sometimes more. Leaf shape: Ovate to elliptic. Leaf blade size: 7–8 cm.×2.5–3 cm. Leaf margin: Ciliated and slightly serrated. Leaf texture: Slightly undulant. (a) Upper surface: Glabrous, with setose mid-vein. (b) Under surface: Glabrous, slightly setose on veins. Leaf color: Dark green. (a) Upper surface: Green, darker than R.H.S. 139A. (b) Under surface: Light green, between R.H.S. 138A and R.H.S. 191A. Venation: Pinnate with reddish-green mid-vein.

Flowering description:

*Flowering habit.*—Very floriferous, floweirng continuously. Flowers develop progressively around the whorl of leaves, taking 5-7 days from buds which show color to bloom. Flowers are single and large, lasting for 2-3 weeks.

*Natural flowering season.*—Flowering is indeterminate and occurs throughout the year. Quantity of flowers increases with increasing light intensity and duration.

*Flower buds.*—Ellipsoidal and covered with 5 sepals. A reddish, approximately 4.5 cm long spur originates from the base of the major sepal. Two smaller sepals are on either side of the spurred sepal and two additional, rudimentary sepals are fused to back of the top petal.

*Flowers borne.*—Singly, on pedicels 3-3.5 cm. long and reddish in color.

*Quantity of flowers.*—Floriferous. One flower per leaf occurring progressively around the whorl of leaves so that tight buds to mature blooms are visible at the same time in large numbers.

*Petals.*—Number of petals: Five (5). Shape: Top petal heart shaped with wide base, all other petals heart shaped with pointed base. All petals overlap, except the bottom two which only touch or slightly overlap. Color: Upper surface: Dark velvety red, darker than R.H.S. 46B, near R.H.S. 45A. Under surface: Orange-red, near R.H.S. 40A. Size of flowers: 5 cm. diameter.

*Reproductive organs.*—Stamens: Five (5), with the lower stamen being shorter than the other stamens. Stamens are united in an asymmetrical tube surrounding the ovary. Anthers: Hooded, cream fused with red. Pollen: Cream color. Stigma: Five pointed star, creamy white. Styles: Very short, reddish in color. Ovary: 5 celled, 5 mm. long until fertilized, green in color.

I claim:

1. A new and distinct cultivar of Impatiens plant named Anaea, as illustrated and described.

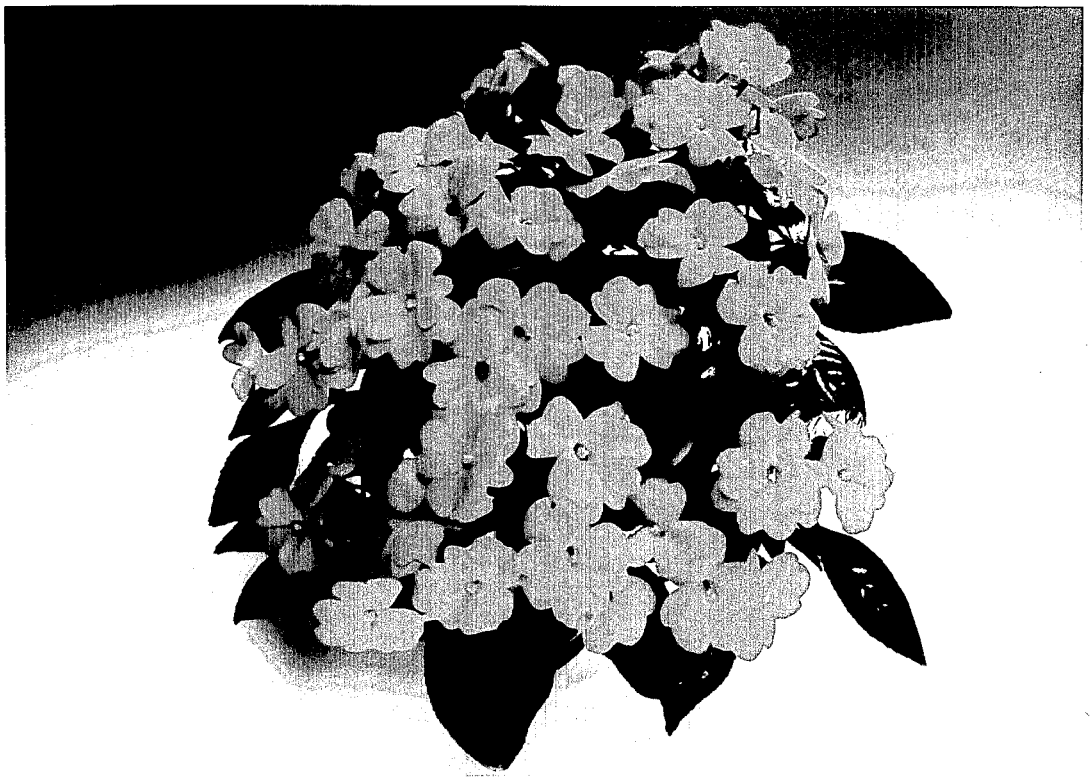

* * * * *